United States Patent

Winkelmann et al.

[11] 3,984,560
[45] Oct. 5, 1976

[54] COMPOSITION FOR AND METHOD OF TREATING DISEASE CAUSED BY PROTOZON

[75] Inventors: Erhardt Winkelmann, Kelkheim, Taunus; Wolfgang Raether, Dreieichenhain, both of Germany

[73] Assignee: Hoechst Aktiengesellschaft, Frankfurt am Main, Germany

[22] Filed: Sept. 4, 1975

[21] Appl. No.: 610,407

Related U.S. Application Data

[62] Division of Ser. No. 470,666, May 16, 1974, Pat. No. 3,907,816.

[30] Foreign Application Priority Data

May 18, 1973 Germany............................ 2325159
June 14, 1973 Germany............................ 2330279

[52] U.S. Cl. .............................................. 424/263
[51] Int. Cl.² ......................................... A61K 31/44
[58] Field of Search ................................... 424/263

[56] References Cited
UNITED STATES PATENTS 3,635,995   1/1972   Manning ...................... 260/294.8 G Primary Examiner—Jerome D. Goldberg
Attorney, Agent, or Firm—Curtis, Morris & Safford

[57] ABSTRACT

This invention provides 1-alkyl-2-(pyridylthiomethyl)-5-nitro-imidazoles and 1-alkyl-2-(N-oxy-pyridylthiomethyl)-5-nitro-imidazoles of the formula

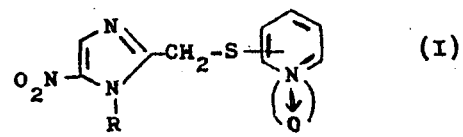

in which R is methyl, ethyl or hydroxyethyl and the pyridyl and N-oxy-pyridyl group is linked in 2-, 3- or 4-position to the sulfur atom, as well as process for the manufacture of these compounds.

The novel compounds are suitable for the treatment of protozoal diseases in mammals.

6 Claims, No Drawings

COMPOSITION FOR AND METHOD OF TREATING DISEASE CAUSED BY PROTOZON

This is a division of application Ser. No. 470,666 filed May 16, 1974, now U.S. Pat. No. 3,907,816 granted Sept. 23, 1975.

The present invention relates to 1-alkyl-2-(pyridylthiomethyl)-5-nitro-imidazoles and derivatives thereof as well as to a process for their manufacture.

1-(2'-Hydroxyethyl)-2-methyl-5-nitroimidazole (Metronidazol) is known to be used for the treatment of protozoal diseases, such as trichomoniasis and amebiasis.

Object of this invention are 1-alkyl-2-(pyridylthiomethyl)-5-nitro-imidazoles and 1-alkyl-2-(N-oxy-pyridylthiomethyl)-5-nitro-imidazoles of the formula I

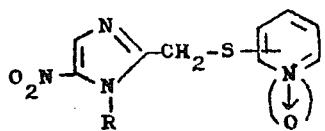

in which R stands for a methyl, ethyl or hydroxyethyl group, and the pyridyl or N-oxy-pyridyl group is linked in 2-, 3- or 4-position to the sulfur atom.

The novel compounds have a pronounced activity against trichomonads and amebae, which activity is superior to the said Metronidazol.

Further object of this invention is a process for the manufacture of 1-alkyl-2-(pyridylthiomethyl)-5-nitro-imidazoles and 1-alkyl-2-(N-oxy-pyridylthiomethyl)-5-nitro-imidazoles of formula I, which comprises a. reacting a 1-alkyl-2-halomethyl-5-nitro-imidazole of the formula II

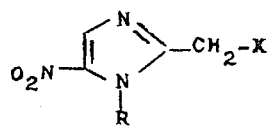

in which R is defined as above, and X stands for a halogen atom, an acyloxy group, preferably acetoxy, propoxy, butoxy, benzoyloxy, benzyloxy or tolyloxy, or an arylsulfonic acid ester group, preferably a benzene-sulfonic acid ester, toluenesulfonic acid ester or naphthalene-sulfonic acid ester group, with a mercaptopyridine or a mercapto-N-oxy-pyridine or the alkali metal or ammonium salt thereof, corresponding to the formula III

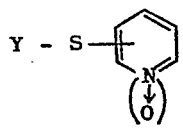

in which Y stands for a hydrogen atom or an alkali metal or ammonium ion, or b. reacting a 1-alkyl-2-mercaptomethyl-5-nitro-imidazole of the formula IV

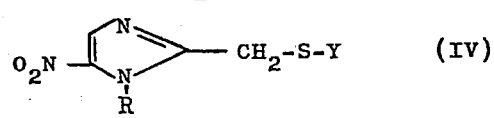

in which R and Y are defined as above, with a halogenopyridine or a halogeno-N-oxy-pyridine of the formula V

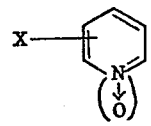

in which X is defined as above.

As compounds of the formula II, 1-methyl-2-chloromethyl-5-nitro-imidazole, 1-methyl-2-bromomethyl-5-nitro-imidazole, 1-methyl-2-iodomethyl-5-nitro-imidazole, 1-ethyl-2-chloromethyl-5-nitro-imidazole, 1-ethyl-2-bromomethyl-5-nitro-imidazole, 1-ethyl-2-iodomethyl-5-nitro-imidazole, 1-(2-hydroxyethyl)-2-chloro-methyl-5-nitro-imidazole, 1-(2-hydroxyethyl)-2-bromomethyl-5-nitro-imidazole and 1-(2-hydroxyethyl)-2-iodomethyl-5-nitro-imidazole or the corresponding methyl-2-phenyl- or 2-toluyl-sulfonates are preferably used.

As compounds of the formula III, 2-, 3- or 4-mercaptopyridine as well as 2-, 3- or 4-mercapto-N-oxy-pyridine or the alkali metal or ammonium salts thereof are preferably used.

Instead of the mercapto compounds, compounds which yield mercaptanes, for example isothiouronium salts, may also be used.

As compounds of the formula IV, 1-methyl-, 1-ethyl- or 1-(2-hydroxyethyl)-2-mercaptomethyl-5-nitro-imidazoles or the alkali metal or ammonium salts thereof are preferably used.

Instead of the mercapto compounds, compounds which yield mercaptanes, for example isothiouronium salts, may also be used.

As compounds of the formula V, 2-, 3-, 4-chloropyridine, 2-, 3-, 4-bromo-pyridine or 2-, 3-, 4-iodo-pyridine as well as 2-, 3-, 4-chloro-N-oxy-pyridine, 2-, 3-, 4-bromo-N-oxy-pyridine, 2-, 3-, 4-iodo-N-oxy-pyridine or the corresponding benzene- or toluene-sulfonic acid esters are preferably used.

The reactions are advantageously carried out in equimolar amounts of the reactants in a solvent or dispersing agent. Depending on the mode of operation, an unpolar or polar aprotic solvent is used. As unpolar solvents, benzene, toluene, xylene and chlorobenzene are used. As aprotic solvents, pyridine, picoline, quinoline, dimethylformamide, dimethylacetamide, N-methylpyrrolidone, tetramethyl-urea, hexamethylphosphoric acid triamide and dimethylsulfoxide are used.

Depending on the mode of operation chosen, the reaction temperatures may be in the range of from 0° to 200°C. In unpolar solvents, they are advantageously in the range of from 50° to 150°C and in aprotic solvents in the range of from 100° to 150°C. The reaction times are in the range of from a few minutes to several hours, depending on the mode of operation.

When the free mercapto compounds of formulae III and IV are used, it is advantageous to use an acid-binding agent, for example a base, such as triethylamine or pyridine, or an alkali metal or alkaline earth metal carbonate or bicarbonate, hydroxide or alkoxide, for example alkali metal or alkaline earth metal methoxide, ethoxide or butoxide.

The products of the invention are isolated by usual methods, depending on the mode of operation, either by distillation of the solvent used or by dilution of the reaction solution with water. Where required, they may be purified by recrystallizing them from a suitable solvent or mixture of solvents.

The 1-alkyl-2-(pyridylthiomethyl)-5-nitro-imidazoles and the 1-alkyl-2-(N-oxy-pyridylthiomethyl)-5-nitro-imidazoles are suitable for the treatment of protozoal diseases in mammals, for example those diseases caused by infections with Trichomonas vaginalis and Entamoeba histolytica. The novel products of the invention may be administered by the oral or local route. For the oral administration, the products are generally made into tablets or capsules containing, per daily dosage unit, about 10 to 750 mg of the active ingredient, in admixture with a usual diluent and/or excipient, for example starch, lactose, finely divided silicic acid, talcum, magnesium stearate or calcium carbonate. For a local or topical application, jellies, creams, ointments or suppositories may be used.

In addition to a good compatibility, the compounds of the invention are distinguished by a safe activity against trichomonads and amebae in vivo, which activity is substantially superior to the known pharmaceutical composition Metronidazol, as can be seen from the following Tables.

The following Examples illustrate the invention.

EXAMPLE 1 (test for activity):

Activity against *Trichomonas foetus* was generally tested on home-bred albino mice (NMRI-strain) of both sexes. The body weight of each animal was from 10 to 12 grams.

The substance to be tested was administered orally by means of an oesophagal sound either in an aqueous solution or, in the case of sparingly water-soluble compounds, in a Tylose suspension. The overall dosage was administered in two units, the first 2 hours prior to infection and the second 2 hours after infection. 4 Mice were used for each substance to be tested and for each dosage.

Infection was brought about by intraperitoneal injection of 19 million infective agents per animal in a suspension in 0.5 ml of a culture medium, Merck I. The comparison preparation Metronidazol was administered by the same route and in the same dosage as the substance to be tested (see Table I).

As infection controls there were generally used 10 mice which, after infection, were not treated any more. Another 5 mice served as a zero control, that is to say, these animals were neither treated nor infected.

Six days after infection, all the test animals were killed and the peritoneal exudate was examined for trichomonads. Mice which had died before were subjected to the same examination.

The tested substance was judged on the concentration of infective agents to be found in the peritoneal exudate on the 6th day after infection. For this purpose, the concentration of infective agents established with the tested composition was compared with that of the comparison preparation and of the infection control. The scheme, according to which the tested substance and the standard were judged with regard to the concentration of infectants established, was the following:

ineffective: Concentration of infective agents was not substantially reduced as compared to infection control. Judgement: 3; 4 effective:
  a. faint: Concentration of infective agents was moderately reduced compared with infection control. Judgement: 2
  b. unsatisfactory: Concentration of infective agents was substantially reduced compared with infection control. Judgement: 1
  c. no infective agents found. Judgement: 0

TABLE 1

| Composition | dosage in mg/kg mouse, per os | Concentration of infectant *Trichomonas Foetus* in 4 mice |
|---|---|---|
| I | 2 × 100 | 0 0 0 0 |
|   | 2 × 50  | 0 0 0 0 |
|   | 2 × 25  | 0 0 0 0 |
|   | 2 × 12.5| 0 0 0 0 |
| II | 2 × 100 | 0 0 0 0 |
|   | 2 × 50  | 0 0 0 0 |
|   | 2 × 25  | 2 0 2 2 |
|   | 2 × 12.5| 4 3 4 4 |
| infection controls | — | 4 4 4 4 |

I = product of the invention: 1-methyl-2-(2'-pyridylthiomethyl)-5-nitro-imidazole
II = comparative composition: Metronidazol

EXAMPLE 2 (test for activity):

Activity against *Entamoeba histolytica* was generally tested on cross-bred golden hamsters of both sexes. The body weight of each animal was generally in the range of from 50 to 60 grams.

The substance to be tested was administered orally by means of an oesophagal sound, either in an aqueous solution or, in the case of sparingly water-soluble compounds, in a Tylose suspension. The overall dosage was administered in four units, the first two hours prior to infection, the second two hours after infection, the third one day after infection and the fourth two days after infection. 4 Hamsters were used for each substance to be tested.

Infection was brought about by intrahepatic injection of 130,000 infective agents per animal as a suspension in 0.1 ml of TTY medium (*E. hist.-Crithidia* culture). The standard Metronidazol was administered by the same route and in the same dosage as the substance to be tested (see Table 2).

As infection controls there were generally used 10 hamsters which were, after infection, not treated any more. Another 5 hamsters served as a zero control, that is to say, these animals were neither treated nor infected.

Six days at the earliest and eight days at the latest after infection, all the animals were killed. Subsequently, the state of the liver was judged according to the degree of icteric necrosis developed. Hamsters which had died during the period of infection were subjected to the same examination.

The observations on the state of the liver obtained with the tested composition and with the standard were compared with those of the infection controls. The scheme, according to which the liver findings (with tested composition and standard) were judged, was the following:

ineffective: Icteric necrosis did not show any substantial difference from that of infection controls. Possible judgement: 3; 4 (in rare cases: 2), effective:
a. faint: Icteric necrosis was less developed than with the infection controls. Possible judgement: frequently 2 (in rare cases: 1),
b. unsatisfactory: Icteric necrosis was substantially reduced as compared to infection controls. Possible judgement: 0 (in rare cases), predominantly 1; 2 (in rare cases),
c. good: no icteric necrosis was discovered. Judgement: 0

TABLE 2

| Composition | dosage in mg/kg golden hamster, per os | liver findings Entamoeba histolytica (extraintestinal) in 4 golden hamsters |
|---|---|---|
| I | 4 × 100 | 0 0 0 0 |
|  | 4 × 50 | 0 0 0 0 |
|  | 4 × 25 | 0 0 0 0 |
| II | 4 × 100 | 0 0 0 0 |
|  | 4 × 50 | 0 1 0 0 |
|  | 4 × 25 | 2 0 2 0 |
| infection controls | — | 4 4 4 4 |

I = Product of the invention: 1-methyl-2-(2'-pyridylthiomethyl)-5-nitro-imidazole
II = comparative composition: Metronidazol EXAMPLE 3 (preparation of active substances):

1. 1-Methyl-2-(2'-pyridylthiomethyl)-5-nitro-imidazole 2.3 Grams (0.1 mol) of metallic sodium were dissolved in small portions in 50 ml of anhydrous methanol. Into this sodium methylate solution, 11.0 g (0.1 mol) of 2-mercaptopyridine dissolved in 70 ml of anhydrous methanol were introduced and the solution was evaporated in vacuo. A solution of 17.55 g (0.1 mol) of 1-methyl-2-chloromethyl-5-nitro-imidazole in 100 ml of dimethylacetamide was added to the residue, and the reaction mixture was heated to 110°C for 1 hour. After cooling, water was added to the solution until crystallization began. The end product was suction-filtered and recrystallized from ethanol with the addition of charcoal. 20.0 Grams of 1-methyl-2-(2'-pyridylthiomethyl)-5-nitro-imidazole were thus obtained (corresponding to 80 % of the theoretical yield) in the form of yellowish crystals, m.p. 147°C. In the same manner there were obtained, with good yields, 2. 1-Methyl-2-(3'-pyridylthiomethyl)-5-nitro-imidazole from 1-methyl-2-chloromethyl-5-nitro-imidazole and 3-mercaptopyridine.

3. 1-Methyl-2-(4'-pyridylthiomethyl)-5-nitro-imidazole (m.p. 143°C) from 1-methyl-2-chloromethyl-5-nitro-imidazole and 4-mercapto-pyridine.

4. 1-Methyl-2-(N-oxy-2'-pyridylthiomethyl)-5-nitro-imidazole (m.p. 257°C with decomposition) from 1-methyl-2-chloromethyl-5-nitro-imidazole and 2-mercaptopyridyl-N-oxide.

5. 1-Methyl-2-(N-oxy-3'-pyridylthiomethyl)-5-nitro-imidazole from 1-methyl-2-chloromethyl-5-nitro-imidazole and 3-mercaptopyridyl-N-oxide.

6. 1-Methyl-2-(N-oxy-4'-pyridylthiomethyl)-5-nitro-imidazole (m.p. 250°C with decomposition) from 1-methyl-2-chloromethyl-5-nitro-imidazole and 4-mercaptopyridyl-N-oxide.

7. 1-Ethyl-2-(2'-pyridylthiomethyl)-5-nitro-imidazole (m.p. 68°C) from 1-ethyl-2-chloromethyl-5-nitro-imidazole and 2-mercaptopyridine.

8. 1-Ethyl-2-(3'-pyridylthiomethyl)-5-nitro-imidazole from 1-ethyl-2-chloromethyl-5-nitro-imidazole and 3-mercaptopyridine.

9. 1-Ethyl-2-(4'-pyridylthiomethyl)-5-nitro-imidazole (m.p. 64°C) from 1-ethyl-2-chloromethyl-5-nitro-imidazole and 4-mercapto-pyridine.

10. 1-ethyl-2-(N-oxy-2'-pyridylthiomethyl)-5-nitro-imidazole (m.p. 176°C) from 1-ethyl-2-chloromethyl-5-nitro-imidazole and 2-mercaptopyridyl-N-oxide.

11. 1-Ethyl-2-(N-oxy-3'-pyridylthiomethyl)-5-nitro-imidazole from 1-ethyl-2-chloromethyl-5-nitro-imidazole and 3-mercapto-pyridyl-N-oxide.

12. 1-Ethyl-2-(N-oxy-4'-pyridylthiomethyl)-5-nitro-imidazole (m.p. 167°C) from 1-ethyl-2-chloromethyl-5-nitro-imidazole and 4-mercaptopyridyl-N-oxide.

13. 1-(2-Hydroxyethyl)-2-(2'-pyridylthiomethyl)-5-nitro-imidazole (m.p. 105°C) from 1-(2-acetoxyethyl)-2-chloromethyl-5-nitro-imidazole and 2-mercaptopyridine with subsequent saponification of the acetyl group.

14. 1-(2-Hydroxyethyl)-2-(3'-pyridylthiomethyl)-5-nitro-imidazole from 1-(2-acetoxyethyl)-2-chloromethyl-5-nitro-imidazole and 3-mercaptopyridine and subsequent saponification of the acetyl group.

15. 1-(2-Hydroxyethyl)-2-(4'-pyridylthiomethyl)-5-nitro-imidazole (m.p. 98°C) from 1-(2-acetoxyethyl)-2-chloromethyl-5-nitro-imidazole and 4-mercaptopyridine and subsequent saponification of the acetyl group.

16. 1-(2-Hydroxyethyl)-2-(N-oxy-2'-pyridylthiomethyl)-5-nitro-imidazole from 1-(2-acetoxyethyl)-2-chloromethyl-5-nitro-imidazole and 2-mercaptopyridyl-N-oxide and saponification of the acetyl group.

17. 1-(2-Hydroxyethyl)-2-(N-oxy-3'-pyridylthiomethyl)-5-nitro-imidazole from 1-(2-acetoxyethyl)-2-chloromethyl-5-nitro-imidazole and 3-mercaptopyridyl-N-oxide and saponification of the acetyl group.

18. 1-(2-Hydroxyethyl)-2-(N-oxy-4'-pyridylthiomethyl)-5-nitro-imidazole from 1-(2-acetoxyethyl)-2-chloromethyl-5-nitro-imidazole and 4-mercaptopyridyl-N-oxide and saponification of the acetyl group.

Preparation of the starting substances

The 1-alkyl-2-chloromethyl-5-nitro-imidazoles used as starting substances were prepared according to known methods by reacting 1-alkyl-2-hydroxymethyl-5-nitro-imidazoles with thionyl chloride.

19. 26.1 Grams (0.1 mol) of 1-methyl-2-benzoyloxymethyl-5-nitro-imidazole were dissolved while stirring in 150 ml of dimethylformamide; then 11.1 g (0.1 mol) of 2-mercaptopyridine and 13.8 g of potash (free from water and powdered) were added. A very faintly exothermic reaction was perceptible only. The reaction mixture was heated to 80°C for 1 hour, whereupon the color of the mixture changed from yellow toward light brown and a white precipitate formed. The mixture was then cooled to room temperature and the end product was precipitated by stirring it into about 500 ml of ice water. The product was suction-filtered, thoroughly washed with water and recrystallized from about 3000 ml of isopropanol. 18.0 Grams (72 % of the theoretical yield) of 1-methyl-2-(2-pyridylthiomethyl)-5-nitro-imidazole were obtained as a faintly yellow crystallized powder, m.p. 146°–147°C.

The 1-methyl-2-benzoyloxymethyl-5-nitro-imidazole used as starting material was prepared by reacting 1-methyl-2-hydroxy-methyl-5-nitro-imidazole with benzoyl chloride in the presence of a hydrogen chloride-binding agent, such as, for example pyridine, m.p. 108°C.

20. The reaction of equimolar amounts of 1-methyl-2-(S-isothiouronium-methyl)-5-nitro-imidazole hydrochloride and 2-bromo-pyridine in dimethylformamide in the presence of 2 molar equivalents of sodium methylate with stirring for 1 hour at room temperature yielded 1-methyl-2-(2-pyridylthiomethyl)-5-nitro-imidazole, m.p. 147°C.

The 1-methyl-2-(S-isothiouronium-methyl)-5-nitro-imidazole hydrochloride used as starting material was used instead of the free, unstable 1-methyl-2-mercaptomethyl-5-nitro-imidazole as a possible mercaptane-forming agent. The preparation of 1-methyl-2-(S-isothiouroniummethyl)-5-nitro-imidazole hydrochloride from 1-methyl-2-chloromethyl-5-nitro-imidazole and thiourea has been disclosed in German Offenlegungsschrift No. 2,124,103 (cf. Merck Inc., Rahway).

We claim:

1. A pharmaceutical composition for treatment of diseases caused by protozoa, consisting essentially of about 10 to 750 mg per daily dosage unit of an active compound of the formula

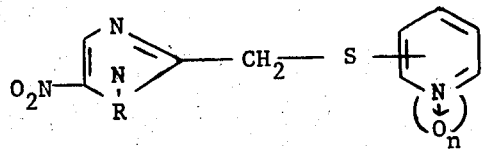

in which R stands for methyl, ethyl or hydroxyethyl, $n$ is 0 or 1 and the pyridyl or N-oxy-pyridyl group is linked in 2-, 3- or 4-position to the sulfur atom in admixture with a pharmaceutical carrier.

2. A composition as defined in claim 1 in which the active compound is 1-methyl-2-(2'-pyridylthiomethyl)-5-nitroimidazole.

3. An oral dosage unit for treatment of diseases caused by protozoa consisting essentially of about 10 to 750 mg of an active compound of the formula

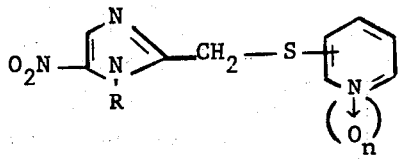

in which R stands for methyl, ethyl or hydroxyethyl, $n$ is 0 or 1 and the pyridyl or N-oxy-pyridyl group is linked in 2-, 3- or 4-position to the sulfur atom in admixture with a pharmaceutical carrier.

4. An oral dosage unit as defined in claim 3 in which the active compound is 1-methyl-2-(2'-pyridylthiomethyl)-5-nitroimidazole.

5. Method of treatment of diseases caused by protozoa which comprises administering to a patient a daily dosage of about 10 to 750 mg of an active compound of the formula

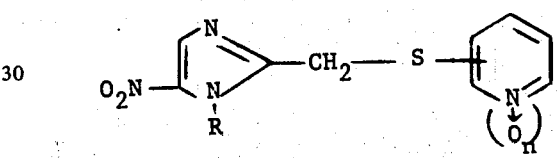

in which R stands for methyl, ethyl or hydroxyethyl, $n$ is 0 or 1 and the pyridyl or N-oxy-pyridyl group is linked in 2-, 3- or 4-position to the sulfur atom in admixture with a pharmaceutical carrier.

6. Method of treatment defined in claim 5 in which the active compound is 1-methyl-2-(2'-pyridylthiomethyl)-5-nitro-imidazole.

* * * * *